United States Patent
Cohen

(10) Patent No.: US 6,568,398 B2
(45) Date of Patent: May 27, 2003

(54) METHOD FOR HEMOSTASIS

(75) Inventor: Edgar C Cohen, New Orleans, LA (US)

(73) Assignee: Edgar C. Cohen, New Orleans, LA (US)

( * ) Notice: Subject to any disclaimer, the term of this patent is extended or adjusted under 35 U.S.C. 154(b) by 97 days.

(21) Appl. No.: 09/799,693

(22) Filed: Mar. 7, 2001

(65) Prior Publication Data

US 2002/0169476 A1 Nov. 14, 2002

(51) Int. Cl.$^7$ .................................................. A61B 19/00
(52) U.S. Cl. ........................ 128/898; 424/499; 424/435; 428/402.24; 264/4
(58) Field of Search ........................ 424/435, 444, 424/447, 49; 604/289, 290; 128/898

(56) References Cited

U.S. PATENT DOCUMENTS

| | | |
|---|---|---|
| 3,869,406 A | 3/1975 | Matsukawa |
| 3,872,024 A | 3/1975 | Horger |
| 3,878,121 A | 4/1975 | Roche |
| 4,394,287 A | 7/1983 | Scarpelli |
| 4,395,398 A | 7/1983 | Yamamoto |
| 4,413,987 A | 11/1983 | Schwartz |
| 4,551,100 A | 11/1985 | Fischer |
| 4,597,960 A | 7/1986 | Cohen |
| 4,617,950 A | 10/1986 | Porteous et al. |
| 4,778,679 A | 10/1988 | Silvetti |
| 5,250,569 A | 10/1993 | Godfrey |
| 5,454,719 A | 10/1995 | Hamblen |
| 5,635,162 A | 6/1997 | Fischer |
| 5,773,033 A | 6/1998 | Cochrum et al. |
| 5,785,955 A | 7/1998 | Fischer |
| 5,830,197 A | 11/1998 | Rucinski |
| 6,050,981 A | 4/2000 | Lampropoulos et al. |

OTHER PUBLICATIONS

Kirk and Othmer *Encyclopedia Of Chemical Technology* 2nd. Edition , vol. 13 Microencapsulation pp. 436–456.

Primary Examiner—Weilun Lo
Assistant Examiner—Linh Truong
(74) Attorney, Agent, or Firm—Millen, White, Zelano, Branigan, P.C.

(57) ABSTRACT

This invention relates to hemostatic therapeutic compositions and, more particularly to methods for bringing about rapid, painless hemostasis intraorally, for dermatological applications or all other hemostasis applications.

100 to 300 micron microcapsules comprising a granular astringent hemostatic agent micro-encapsulated with a biocompatible polymer are applied to a wound. The microcapsules are applied to the wound until the outermost layer of microcapsules remain white, a visible indication that the hemostatic action is complete. Upon observation that the hemostatic action is complete the microcapsules are flushed from the wound, the wound blotted and dressed. The rapid clotting times achieved with the 100 to 300 micron size microcapsules together with the visual indication that hemostasis is complete gives the practitioner the ability to irrigate the wound and apply a protective dressing much more quickly than the prior art and excess microcapsules are not wasted.

16 Claims, No Drawings

METHOD FOR HEMOSTASIS

This invention relates to methods for bringing about rapid, painless hemostasis intraorally, for dermatological applications or all other hemostasis applications.

A present method for effecting hemostasis intraorally involves the direct application of an astringent solution to the gingival crevice. A problem associated with the use of present astringent solutions is that they generally rapidly flow away from the gingival crevice and do not sustain their astringent action for an adequate period of time. Use of readily washed away astringent solutions is often ineffective for bringing about adequate hemostasis.

For intraoral, dermatological and all other hemostasis applications, present astringent and hemostatic materials for application to body tissues are comprised of active ingredients which immediately react with the body tissues upon contact therewith. If a practitioner applies an excessively large quantity of such material to the tissues, then those tissues are immediately subjected to an excessively large quantity of reactive agent. A problem that may result from such an occurrence is that delicate tissues may be irritated by the excess astringent substances, and excess astringent is wasted.

There are various hemostasis and astringents which have been used to control bleeding. One of the most common hemostatic and retraction agents used in dentistry is an aqueous solution of 25% aluminum chloride marketed under a variety of tradenames including Denti-Care Hemostat, Hemodent, Hemoban, and Gingi Aid. Ferric salts have also been used as astringents, such as Monsel's solution which is based on ferric subsulfate, ferric sulfate, and ferric chloride. U.S. Pat. No. 4,617,950, discloses an astringent gel which includes an astringent salt and a bodying agent such as carboxypolymethylene. U.S. Pat. No. 4,551,100 teaches a aqueous ferric sulfate solution for use in the gingival area as a hemostatic agent having both coagulant and astringent properties. U.S. Pat. No. 5,454,719 provides a sterile gauze dental pack which provides hemostasis by direct pressure. U.S. Pat. No. 4,395,398 deals with an aqueous dental hemostatic composition comprising one or more astringents and a surfactant in a carrier or diluent. U.S. Pat. No. 4,597,960 discloses powdered astringent hemostasis agents microencapsulated with a hemostatic polymer. A variety of different particle size astringent hemostatic agents are encapsulated in capsules having a variety of capsule wall thickness. U.S. Pat. Nos. 5,635,162 and 5,785,955 relate hemostatic compositions for controlling oral bleeding. The compositions includes a hemostatic agent, an agent to reduce the acidic activity of the hemostatic agent, and an aqueous base. U.S. Pat. No. 5,773,033 concerns fibrinogen and chitosan hemostatic adhesive agents which can be topically applied to bleeding wounds or vessels.

Another typically used hemostatic agent is Kaltostat which is composed of the sodium and calcium salts of alginic acid. The dressing is generally in the form of a non-woven pad consisting of absorbent fibrous fleece for application to surface wound or other body fluids. As the fibers absorb liquid and swell the dressing to takes on a gel-like appearance.

The present art of bandages to be applied topically to skin surfaces discloses astringent hemostatic agents impregnated into bandage substrate materials. However, there are problems associated with such bandages which are similar to problems associated with conventionally impregnated gingival retraction cords relating to an excess of astringent agent being applied to delicate body tissues. There are no bandages presently impregnated with astringent agents that are released only upon demand.

The hemostasis action of fibrin glue has been demonstrated. Thrombin is present in the fibrin glues, which are generally prepared from pooled human and bovine blood. The non-human antibodies present, sometimes result in severe anaphylactic reactions and there is a possibility of transmitting infectious disease from the human components. Additionally, purified or biocompatible fibrin compositions are extremely expensive.

In accordance with one aspect of this invention, a novel method is provided for producing rapid, painless hemostasis and which provides a visual color indication upon completion of hemostasis. The methods of the invention may be used for intraoral, dermatological and all other hemostasis applications. The composition is comprised of a powdered astringent hemostatic agent microencapsulated with a polymer that has hemostatic properties, is biologically inert; is compatible with human tissue; and, is non-allergenic. The particle size distribution of the individual microcapsules are preferably in the range of about 100 to 300 micron, more preferably in the range of about 200 to 250 micron, and most preferably containing less than 10% of particle above the upper range limits. In practice the hemostatic granules are applied over the wound or bleeding surface until coagulation occurs, at which point the last layer of granules will remain white and the granules may be washed from the wound or cut. The granules of the invention may be used alone or in combination with other agents or techniques typically used to facilitate hemostasis.

The microencapsulated granules used in the present invention preferably consist of ethyl cellulose encapsulating the astringent. The ethyl cellulose granules accommodate a volume of fluid equal to the volume of the granules. Fluid is both absorbed at the bead interstices and adsorbed at the bead surface. The large surface area of the applied granules fosters coagulation. Within the interior spaces of the ethyl cellulose granules, the aluminum sulfate is dissolved by absorbing fluid. The dissolved astringent diffuses out of the encapsulating granules and produces an astringent action within the wound site which arrests secretion and stops minor bleeding. The granules interacting with the wound appear reddish because of the absorbed exudate and blood. When the hemostatic action is complete the granules remain white and can be rinsed from the tissue. In one preferred embodiment, the astringent is aluminum sulfate, the same as that found in styptic pencils, however the encapsulation of aluminum sulfate with 6% ethyl cellulose reduces the rate of plasma absorption of aluminum by 70% compared to styptic pencil. Extended exposure to the granules of the invention results in negligible increased absorption due to the astringent action of the granules. The product does not cause skin irritation, skin sensitization, acute systemic toxicity, cytotoxicity or hemolysis and does not effect the rate of would healing. Extended exposure to the granules should result in negligible increased absorption of astringent in the plasma due to the astringent action of the granules, however the color change gives the practitioner a visible indication that minor bleeding and secretion have been arrested. The microcapsules can then be irrigated from the wound without subjecting the patient to time delays or wasting astringent microcapsules. Water or any other conventional irrigation solutions and devices such as those found in U.S. Pat. Nos. 5,830,197, 4,778,679, 4,413,987, and 6,050,981, may be used for wound irrigation.

Fine 250 micron, biocompatible granules that contain an astringent such as aluminum sulfate are sprinkled into fresh, minor cuts or superficial wounds to absorb body fluid and to stop minor bleeding in fresh traumatic superficial lacerations or wounds. Once exudation and bleeding has stopped, the outermost layer of microcapsules remain white, are irrigated from the wound and a protective dressing can be applied. For high pressure bleeding, slight pressure may be applied to the microcapsules with gauze pads.

When used intraorally the method of the invention may be used to bring about both gingival retraction and hemostasis. For intraoral applications the preferred microencapsulated astringent hemostatic agent is aluminum sulfate and the preferred encapsulation material is ethyl cellulose. Other microencapsulated astringents may be selected from the group consisting of ferric sulfate, aluminum chloride, and the like.

The methods of the present invention may be used for rapid hemostasis and anti-microbial activity in the wound care and decubitus market or in trauma situations. Applications include medic's kits for military and civilian environments such as hospitals, ambulance, squad cars, fire engines, paramedic units, schools, prisons, nursing homes, asylums, offices, clinics, hospitals, operating rooms, transport vessels, aircraft, and wherever standard armamentarium would be found. The kits may contain sterile containers or packets of the hemostatic micro-capsules and directions of use according to the present invention, along with other typical first aid components. The sterile containers are ready to use and require no mixing, soaking, measuring or cumbersome procedures which can result in the loss of valuable time and excessive hemorrhage.

The micro-capsules of the present invention possess antibacterial properties. 250 micron (6% ethyl cellulose 94% aluminum sulfate) micro-capsules were tested against cultures of five of the most common aerobic pathogens in surgical wound infections and shown to exhibit bactericidal and bacteriostatic activity.

The microencapsulated astringent hemostatic agent of the invention serves to release the active agent from the micro-capsules in a time-release manner. A variety of different particle size astringent hemostatic agents may be encapsulated in capsules having a variety of capsule wall thickness, however the thinner the wall and the smaller the particle, the more rapid the clotting. Additionally, the encapsulation of aluminum sulfate with about 6% ethyl cellulose reduces the rate of plasma absorption of aluminum sulfate and the release of active agent from microcapsules may be sustained at a controlled rate over an extended period of time.

In accordance with another aspect of the invention, a method is provided for bringing about gingival retraction and hemostasis wherein the time-released astringent hemostatic agent of the invention is introduced into the gingival sulcus. When the time-released astringents are inside the gingival sulcus, the active astringent reagent contacts the gingival tissue only when the inner reagent is released. Thus, the time-release astringent act solely on a demand basis; that is, the greater the amount of capillary hemorrhage or bleeding the more astringent reagent is released and directly contacts the gingival tissue to produce clotting and capillary closure.

The mass of time-release astringent hemostatic agent introduced into the wound may be compacted and acts as a gentle, atraumatic, and non-structural mechanical hemostatic astringent means. The compaction of time-released microcapsules may be brought about by compaction with a hand instrument or slight pressure from a hand or bandage until such time as the outermost layer of microcapsules remain white and bleeding has been arrested.

DETAILED DESCRIPTION OF THE INVENTION

For oral use the preferred composition of the invention which produces rapid, painless hemostasis is comprised of 250 micron aluminum sulfate granules encapsulated with a biologically inert and non-allergenic hemostatic polymer such as ethyl cellulose. It is desirable for the hemostasis time to be as short as possible.

For dermatological or other hemostatic use the preferred composition of the invention which produces rapid, painless hemostasis is comprised of 250 micron aluminum sulfate granules encapsulated with a biologically inert and non-allergenic hemostatic polymer such as ethyl cellulose. It is desirable for the hemostasis time to be as short as possible to reduce excessive hemorrhage.

Conventional techniques for preparing astringent particles microencapsulated with a biologically compatible polymer are well known in the art. Teachings of microencapsulation techniques are provided in "Microencapsulation" by Herbig in the Encyclopedia of Chemical Technology, 2nd Edition, Volume 13, published by Kirk-Othmer.

100 to 350 micron microcapsules are the preferred size for use in the method of the present invention and are prepared with a conventional coacervation technique, such as found in U.S. Pat. Nos. 4,394,287; 3,878,121; 3,872,024; and 3,869,406. The term coacervation describes the phenomenon of phase separation. From a homogeneous solution of polymer, droplets of a polymer in liquid form, rather than solid aggregates. This phase, separated in the form of liquid and amorphous droplets, is the coacervate. In preparing the preferred microcapsules used in the present invention, the aluminum sulfate is milled and sieved to obtain granule size of less than 350 microns, and tumbled with the ethyl cellulose and a solvent to form the encapsulated granules.

Other astringent materials that may be microencapsulated in accordance with the invention include aluminum chloride, ferric sulfate, ferric subsulfate, ferric chloride, zinc chloride, aluminum chlorohydrate, aluminum acetate, alum, tannins, permanganates and mixtures thereof. Any other astringents such as those disclosed in U.S. Pat. No. 5,250,569 may also be used in the methods of the present invention.

The preferred wall forming encapsulation material, ethyl cellulose, is biologically inert; is compatible with human tissue; is non-allergenic; and has hemostatic properties. Ethyl cellulose granules contributes to blood clotting by acting as a situs for clot formation.

In addition to intraoral applications of the novel composition of the invention, the novel compositions of the invention have applicability for hemostasis for dermatological purposes. Astringent hemostatic compositions of the invention suitable for dermatological purposes include 100 to 350 micron microencapsulated aluminum sulfate as above and can include additionally other microencapsulated astringent hemostatic materials. For example, microencapsulated aluminum sulfate and microencapsulated aluminum chloride are suitable astringent hemostatic agents of the invention for dermatological purposes.

In addition to ethyl cellulose, other cellulose-based polymeric materials soluble in body fluids may serve as coatings for encapsulation of the selected astringent hemostatic agent. Ethyl cellulose is an ethyl ether of cellulose. Other related ethers such as methyl cellulose may also be used for encapsulation of the astringent hemostatic agent to produce a composition having time-release properties. Other cellulose ethers have inherent hemostatic properties similar to ethyl cellulose.

In general, oxidized cellulose is a useful class of hemostatic materials. Generally, hemostatic oxidized cellulose materials are also absorbed by body fluids as when used to pack wounds. Some commercial absorbable hemostatic cellulose materials are sold under the names of Oxycel and Hemo-Pak.

Although a wide variety of sizes of astringent hemostatic particles and polymer coating thicknesses of encapsulation material may be used, satisfactory compositions of the invention have been obtained by encapsulating micron-mesh astringent with a 3%–6% solution of ethyl cellulose to create granules having a predominant particle size of less than 350 micron, preferably less than 250 micron and more preferably less than 200 micron Clotting times under one minute can be achieved.

In practice, excess 100 to 350 micron hemostatic granules could be applied to a wound without any concern of overdose since the active principle of hemostatic granules is presented to the bleeding tissue on demand and the action ceases when bleeding stops. However, it is preferable to irrigate the wound once hemostatic action is complete and to apply a protective dressing. The color indication properties of the last layer of microcapsules allow the practitioner to observe when hemostasis is complete, and so unnecessary material is not applied and excess microcapsules are not wasted. In the preferred 250 micron composition, clotting times of under one minute were achieved in a 2 $cm^2$ cut rat liver lobe. It is desirable for the hemostasis time to be as short as possible while still balancing the handling and aesthetic property aspects. The 250 micron size has desirable handling properties, good aesthetics and rapid clotting times. Additionally, the 250 micron size granule can be obtained in economically satisfactory quantities while still achieving rapid clotting times. Balancing of size vs. desirable properties can be achieved with routine experimentation, in view of the present specification.

In another use of the compositions of the invention, the 100 to 350 micron microencapsulated astringent hemostatic agents can be used in conjunction with gingival retraction cord to further enhance retraction and hemostasis. This can be accomplished in two ways: either the microencapsulated astringent hemostatic agent is applied immediately superior to the subgingivally-placed retraction cord after placement in the sulcus, or microencapsulated astringents are contacted with the surface of a previously dampened gingival retraction cord prior to placement of the cord into subgingival areas.

The powdered microencapsulated astringent hemostatic agents of the invention may be used by locally applying an appropriate amount thereof on a bleeding part. For example, if a skin wound were a relatively shallow abrasion over a relatively large skin surface, the practitioner may apply a relatively small amount of a composition of the invention having relatively small amounts of the astringent hemostatic agent because of the relatively small amounts of blood flow. On the other hand, if the skin wound was a deep laceration or tear, a more highly concentrated formulation may be applied by the practitioner to treat the more localized blood flow of a relatively high rate. In both cases, in accordance with the invention, the release of the microencapsulated astringent hemostatic agent from the microcapsules is upon demand depending upon contact with body liquids such as blood and the observation that the last layer of microcapsules remain white indicate that the application is complete.

If the use of the composition of the invention is merely for a short period of time such as for first aid purposes, the practitioner may desire a rapidly released composition of the invention. However, if the applied material is expected to be in use for a considerable length of time, then a formulation having longer time release properties may be employed. The practitioner may vary the microcapsules size to adjust the rate of hemostatic action.

Accordingly, the invention provides a painless and rapid method for providing an active astringent and hemostatic agent on demand for contact with body tissues and, by virtue of its color characteristics, signals when the hemostatic action is complete. Since astringent is presented on demand, delicate tissue is not subjected to excess reagent and tissue irritation is avoided.

Yet another advantage of the invention is the provision of a method and composition for controlling the amount of active hemostatic agent which contacts tissues.

Another advantage of the invention is the provision of a composition and method for applying hemostatic astringent in adequate quantities to tissues or wounds so that the amount is precisely the amount that is needed to effect hemostasis without excess micro-capsules being wasted.

The invention provides for a safe and easy to handle, rapid hemostatic composition which is aesthetically pleasing and which can be manufactured consistently and economically. Additionally the microcapsules of the invention possess bactericidal and bacteriostatic activity against several microorganisms, including some of those most commonly present in surgical wound infections.

In the foregoing and in the following examples, all temperatures are set forth uncorrected in degrees Celsius; and, unless otherwise indicated, all parts and percentages are by weight.

The entire disclosure of all applications, patents and publications, cited above and below are hereby incorporated by reference.

EXAMPLE I

The coagulation times listed below are obtained on liver cuts in anesthetized rats.

Following anesthesia, the tip of a liver lobe is cut creating a wound approximately 2 $cm^2$. Immediately following the cut, the wound is blotted with gauze and a layer of hemostatic 250 micron microcapsules are applied. The microcapsules rapidly turn red with the coagulating blood and additional layers are applied until the outermost layer of mircocapsules remain white, at which point hemostasis is established and the time is noted.

Average Clotting Times (Seconds)

| % COATING | MICROCAPSULE DIAMETER (MICRONS) | | |
|---|---|---|---|
| | 150 | 250 | 350 |
| 4 | 38.7 | 44.2 | 63.8 |
| 6 | 41.4 | 48.5 | 73.9 |
| 8 | 55.7 | 63.3 | 96.2 |
| 10 | 76.9 | 95.2 | 124.4 |

EXAMPLE II 250 micron microcapsules (ethyl cellulose 6%/aluminum sulfate 94%) of the present invention are evaluated on skin shave and punch biopsies on human patients. Following tissue sampling, the micro-capsules are sprinkled on the wound and allowed to remain in place until hemostasis is assured. At this point, the time for hemostasis is noted, and the micro-capsules are flushed from the wound and the wound area blotted. In each case the wound remains free of blood and serious fluid after treatment with granules. The wound is dressed with an antibiotic ointment and bandage. The wounds all heal normally without scabbing. The clinical evaluation is presented below.

| PATIENT | AGE | PROCEDURE | LOCATION | BLEEDING TIME |
|---|---|---|---|---|
| White female | 49 | Shave biopsy | Right Cheek | <60 seconds |
| Black female | 36 | Shave biopsy | Right Abdomen | <45 seconds |
| White female | 42 | Shave biopsy | Right chin | <60 seconds |
| White male | 58 | Shave biopsy | Right forehead | <45 seconds |
| Black male | 32 | Punch biopsy | Right hand | =85 seconds* |

A punch biopsy is about one-quarter of one inch deep. Additional time is required for the microcapsules to reach the source of bleeding. In this case, as well as others, the application of light pressure enhances the rate of hemostasis.

EXAMPLE III

Ability of 250 Micron Micro-capsule and Kaltostat to Stop Minor Bleeding

Procedure

Twenty two rats weighing 142–148 gms are anesthetized with 50 mg/kg B.W. intraperitoneally. The abdominal area is shaved and a midline incision is made through the skin and muscle from the lower abdomen up to the xyphoid process. The liver is exposed, isolated with gauze and the tip of the most prominent lobe is cut, producing a wound of approximately 3 cm long and 0.6 cm wide. Blood from the cut surfaces is collected in capillary tubes for control bleeding evaluation. The cut surface is then blotted and either 250 micron micro-capsule or Kaltostat, sufficient to just cover the wound, is applied. The time to stop bleeding is measured and the number of Kaltostat applications required are noted.

Results

The results of this test are shown in Table V. The average bleeding time of 10 determination with 250 micron micro-capsule is 48 seconds (35–80). Six Kaltostat estimates average 5 minutes: 10 seconds (4:15–6:10) and require 5–8 applications and six controls average 9 minutes: 57 seconds (7:25–12:10).

Conclusion

The data reveal that a single application of 250 micron micro-capsules is six times more effective at stopping minor bleeding than five to eight applications of Kaltostat.

Ability of 250 Micron Micro-capsules and Kaltostat to Stop Minor Bleeding

| | | BLEEDING TIMES | | |
|---|---|---|---|---|
| Animal | Date | 250 Micron microcapsules min:sec | Kaltostat min:sec | Controls min:sec |
| RT-F-S8 | 9/25 | 0:45 | | |
| RT-F-S9 | 9/25 | 0:45 | | 8:40 |
| RT-M-S11 | 9/25 | 0:35 | | 10:15 |
| RT-F-K1 | 10/2 | | 4.55 (7) | |
| RT-M-K4 | 10/2 | 0:35 | | |
| RT-M-C7 | 9/25 | 0:45 | | |
| RT-F-S14 | 10/2 | | 6:10 (7) | |
| RT-M-S19 | 9/18 | | 5:10 (6) | |
| RT-F-C5 | 9/25 | 0:40 | | 7:25 |
| RT-F-K6 | 9/25 | 0:35 | | |
| RT-M-D | 9/25 | 0:45 | | 12:10 |
| RT-F-S21 | 9/13 | 1:15 | | |
| RT-F-S22 | 9/13 | | 4:15 (6) | |
| RT-F-K10 | 9/13 | 1:20 | | |
| RT-M-K14 | 9/19 | | 5:40 (8) | |
| RT-M-K15 | 9/19 | | | 11:35 |
| RT-M-K16 | 9/13 | | 4:50 (6) | |
| RT-F=A | 9/25 | | | 9:40 |
| () = number of Kalostat applications | | 0:48 | 5:10 (6.5) | 9:57 |

EXAMPLE IV

Effect of 250 Micron Micro-capsules on Selected Bacterial Pathogens

| Organism | Amt. of 250 Micron microcapsules (g/30 ml media) | Mode of Action | Cidal time |
|---|---|---|---|
| P. aeruginosa | 0 | none | n/a |
| P. aeruginosa | 0.179 | Bactericidal | 60 |
| P. aeruginosa | 1.416 | Bactericidal | <5 |
| E. fecalis | 0 | none | n/a |
| E. fecalis | 0.129 | none | n/a |
| E. fecalis | 1.403 | Bactericidal | 240 |
| S. aureus | 0 | none | n/a |
| S. aureus | 0.149 | Bacteriostatic | n/a |
| S. aureus | 1.373 | Bacteriostatic | n/a |
| E. coli | 0 | none | n/a |
| E. coli | 0.314 | Bactericidal | 60 |
| E. coli | 1.529 | Bactericidal | <5 |
| MRSA | 1.50 | Bactericidal | <30 |
| MRSA | 0.15 | Bacteriostatic | n/a |

Cidal time represents the approximate number of minutes of exposure to 250 micron micro-capsules an organism undergoes a 4 log reduction in colony forming units per ml in those instances where bactericidal activity is observed.

MRSA ia 4-Methicillin resistant Staph. aurcus Indiana University Hospital isolate number 202634.

Concentrations resulting from the dilution of micorcapsules in 30 ml. of media are considerably less than those resulting form direct application of microcapsules to wounds. Thus, the cidal times listed are significantly prolonged.

The embodiments of the invention set forth above are only representative of broad aspects of the invention, and the invention is not to be deemed limited to the particular embodiments set forth. The scope of the invention is to be defined by the claims appended below.

What is claimed is:

1. A method of treating a wound comprising:
   a) applying to a wound, microcapsules comprising a granular astringent hemostatic agent micro-encapsulated with a biocompatible polymer, and b) removing the microcapsules from the wound after observing the outermost layer of microcapsules remain white, indicating the hemostatic action is complete.

2. A method of treating a wound comprising removing microcapsules from a wound after observing the outermost layer of microcapsules remain white indicating completion of hemostatic action, said microcapsules comprising a granular astringent hemostatic agent micro-encapsulated with a biocompatible polymer, wherein the individual microcapsules are 100 to 300 microns.

3. A method according to claim 1, wherein the individual microcapsules are 100 to 300 microns.

4. A method according to claim 3, wherein the individual microcapsules are from 200 to 250 microns.

5. A method according to claim 4, wherein the individual microcapsules are from 200 to 250 microns, containing less than 10% of the microcapsules above the upper limit range.

6. A method according to claim 1, wherein the biocompatible polymer is selected from the group consisting of ethyl cellulose, methyl cellulose, oxycellulose, or oxidized cellulose.

7. A method according to claim 1, wherein the granular astringent hemostatic agent is ferric sulfate, ferric subsulfate, ferric chloride, zinc chloride, aluminum chloride, aluminum sulfate, aluminum chiorohydrate, aluminum acetate, alum, tannins, permangenates or mixtures thereof.

8. A method according to claim 1, wherein the astringent hemostatic agent is used in an amount of 90 to 98% by weight.

9. A method according to claim 1, wherein said astringent hemostatic agent is used in an amount of 92 to 96% by weight.

10. A method according to claim 1, wherein said biocompatible polymer is from 2 to 10% by weight.

11. A method according to claim 1 wherein said biocompatible polymer is used in an amount of 4 to 8% by weight.

12. A method according to claim 1, further comprising applying a protective dressing to the wound after removing the microcapsules from the wound.

13. A method according to claim 1, further comprising applying pressure to said microcapsules after application to said wound.

14. A method of treating a wound to effect hemostasis comprising applying microcapsules comprising a granular astringent hemostatic agent micro encapsulated with a biocompatible polymer, for a period of time until hemostasis occurs and observing the microcapsules until the outermost layer of microcapsules remain white.

15. A method according to claim 14, wherein the individual microcapsules are 100 to 300 microns.

16. A method according to claim 1, further comprising adjusting a given rate of hemostatic action by varying the particle size of microcapsules.

* * * * *